(12) United States Patent
Li

(10) Patent No.: US 8,520,202 B2
(45) Date of Patent: Aug. 27, 2013

(54) ASYMMETRICAL-NANOFINGER DEVICE FOR SURFACE-ENHANCED LUMINESCENSE

(75) Inventor: Zhiyong Li, Foster City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 194 days.

(21) Appl. No.: 13/233,671

(22) Filed: Sep. 15, 2011

(65) Prior Publication Data

US 2013/0070241 A1 Mar. 21, 2013

(51) Int. Cl.
*G01J 3/44* (2006.01)
*G01N 21/65* (2006.01)

(52) U.S. Cl.
USPC .......................... 356/301; 977/700; 977/701

(58) Field of Classification Search
USPC ................... 356/301; 977/700, 701
See application file for complete search history.

(56) References Cited

U.S. PATENT DOCUMENTS

| | | | |
|---|---|---|---|
| 5,677,196 A | 10/1997 | Herron et al. | |
| 6,193,870 B1 | 2/2001 | Morse et al. | |
| 6,222,619 B1 | 4/2001 | Herron et al. | |
| 6,756,795 B2 | 6/2004 | Hunt et al. | |
| 6,777,244 B2 | 8/2004 | Pepper et al. | |
| 7,158,219 B2 | 1/2007 | Li et al. | |
| 7,236,242 B2 * | 6/2007 | Kamins et al. | 356/301 |
| 7,256,886 B2 | 8/2007 | Cullum et al. | |
| 7,388,661 B2 * | 6/2008 | Li et al. | 356/301 |
| 7,402,531 B1 | 7/2008 | Kuekes et al. | |
| 7,528,948 B2 | 5/2009 | Bratkovski et al. | |
| 7,583,379 B2 | 9/2009 | Zhao et al. | |
| 7,597,814 B2 | 10/2009 | Stasiak et al. | |
| 7,656,525 B2 | 2/2010 | Zhao et al. | |
| 7,667,238 B2 | 2/2010 | Erchak | |
| 7,833,842 B2 | 11/2010 | Williams | |
| 7,960,251 B2 | 6/2011 | Choi et al. | |
| 8,148,294 B2 * | 4/2012 | Wang et al. | 502/347 |

(Continued)

FOREIGN PATENT DOCUMENTS

| | | |
|---|---|---|
| EP | 2058908 | 5/2009 |
| JP | 2000-206048 | 7/2000 |

(Continued)

OTHER PUBLICATIONS

Baldwin, Jean, Norbert Schuhler, Ian S. Butler, & Mark P. Andrews, "Integrated Optics Evanescent Wave Surface Enhanced Raman Scattering (IO-EWSRERS) of Mercaptopyridines on a Planar Optical Chemical Bench: Binding of Hydrogen and Copper Ion", Langmuir, 1996, vol. 12, pp. 6389-6398.

(Continued)

*Primary Examiner* — Layla Lauchman

(57) ABSTRACT

An asymmetrical-nanofinger device for surface-enhanced luminescence. The device includes a substrate, and a plurality of nanofingers coupled with the substrate. The plurality of nanofingers includes a primary nanofinger having a primary active-material cap, and a secondary nanofinger having a secondary active-material cap. An average diameter of the primary active-material cap is substantially greater than an average diameter of the secondary active-material cap. The primary nanofinger and secondary nanofinger of the plurality of nanofingers are to self-arrange into a close-packed configuration with an analyte molecule disposed between the primary active-material cap and the secondary active-material cap. A method for fabricating the asymmetrical-nanofinger device, and an optical apparatus including an optical component that includes the asymmetrical-nanofinger device are also provided.

15 Claims, 7 Drawing Sheets

(56) References Cited

U.S. PATENT DOCUMENTS

| | | | |
|---|---|---|---|
| 8,149,397 B2* | 4/2012 | Lee et al. | 356/301 |
| 8,184,284 B2* | 5/2012 | Ebstein | 356/301 |
| 8,279,435 B2* | 10/2012 | Wang et al. | 356/301 |
| 2003/0077023 A1 | 4/2003 | Troll | |
| 2006/0038990 A1 | 2/2006 | Habib et al. | |
| 2006/0231381 A1 | 10/2006 | Jensen | |
| 2007/0070341 A1 | 3/2007 | Wang et al. | |
| 2008/0017845 A1 | 1/2008 | Drndic | |
| 2008/0024776 A1 | 1/2008 | Bratkovski et al. | |
| 2008/0144026 A1 | 6/2008 | Zhao et al. | |
| 2008/0166706 A1 | 7/2008 | Zhang et al. | |
| 2008/0187648 A1 | 8/2008 | Hart | |
| 2008/0311028 A1 | 12/2008 | Stanbery | |
| 2009/0261815 A1 | 10/2009 | Cairns | |
| 2009/0303472 A1 | 12/2009 | Zhao et al. | |
| 2010/0303722 A1* | 12/2010 | Jin et al. | 424/9.1 |
| 2011/0001118 A1 | 1/2011 | Bhupendra | |
| 2011/0030792 A1 | 2/2011 | Miguez | |
| 2011/0128537 A1 | 6/2011 | Bond et al. | |
| 2012/0107948 A1 | 5/2012 | Li et al. | |
| 2012/0188540 A1* | 7/2012 | Bratkovski et al. | 356/301 |
| 2012/0212733 A1* | 8/2012 | Kodali et al. | 356/301 |

FOREIGN PATENT DOCUMENTS

| | | |
|---|---|---|
| WO | WO-03083480 | 10/2003 |
| WO | WO-2010088585 | 8/2010 |
| WO | WO-2010126640 | 11/2010 |
| WO | WO-2011133143 | 10/2011 |
| WO | WO-2011133144 | 10/2011 |

OTHER PUBLICATIONS

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

Fan et al., "Multilayer Silver Nanoparticles Modified Optical Fiber Tip for High Performance SERS Remote Sensing," 217th ECS Meeting—Vancouver, Canada, Apr. 25-Apr. 30, 2010, J2—Electrochemical Nano/Bio Sensors 2, Abs# 1830.

Fan, J. G. et al., "Integrating Aligned Nanorod Array onto Optical Fibers for SERS Probes," Proc. of SPIE—Nanoengineering: Fabrication, Properties, Optics, and Devices III, vol. 6327, 2006, pp. R-1 to R10.

Gopinath, Ashwin, et al., Deterministic Aperiodic Arrays of Metal Nanoparticles for Surface-enhanced Raman Scattering (SERS), Publication Date: Mar. 2, 2009; vol. 17; on pp. 3741-3753. <http://www.bio-page.org/boriskina/Boriskina_OE2009.pdf>.

Guieu, Valérie, et al. "Multitip-localized enhanced Raman scattering from a nanostructured optical fiber array." The Journal of Physical Chemistry C 113.3 (2008): 874-881.

International Search Report, Mar. 30, 2011, PCT Application No. PCT/US2010/044039, filed Jul. 30, 2010.

Josef Giglmayr, "Nano-Finger Electrodes for the Electro-Optical Generation and Tuning of Gratings at Several Wavelengths", <http://www.ipme.ru/ipme/conf/NN2003/NN2003_Abstracts.pdf> Publication Date: Aug. 30, 2003—Sep. 6, 2003.

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol. 20; on pp. 3533-3538. <http://onlinelibrary.wiley.com/doi/10.1002/adma.200702478/abstract>.

Lucotti et al., "Fiber-optic SERS sensor with optimized geometry," Elsevier, ScienceDirect, Sensors and Actuators B, vol. 121, 2007, 356-364.

PCT International Search Report, Jan. 20, 2011, Hewlett-Packard Development Company, L.P. (PCT/US2010/031790, filed Apr. 20, 2010).

PCT International Search Report, Dec. 23, 2010, Hewlett-Packard development Company, L.P. (PCT/US2010/031809, filed Apr. 20, 2010).

Ren, Hongliang, et al. "The preparation of optical fibre nanoprobe and its application in spectral detection." Optics & Laser Technology 39.5 (2007): 1025-1029.

Segawa, H., et al., "Top-gathering pillar array of hybrid organic-inorganic material by means of self-organization", Applied Physics A—Materials Science & Processing, Mar. 17, 2006, vol. 83, pp. 447-451.

White, Daniel J., et al. "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

Chen, S.Y. et al., Raman Antenna Formed by Molecule/plasmonic Nanostructure Hybrid System, (Research Paper), Conference Paper, Quantum Electronics and Laser Science Conference, May 1, 2011, Baltimore, Maryland.

Du, Y. et al., SERS Enhancement) Dependence on the Diameter and Aspect Ratio of Silver-nanowire Array Fabricated by Anodic Aluminium Oxide Template, (Research Paper). Applied Surface Science, Dec. 30, 2008, pp. 1901-1905, vol. 255, No. 5.

Weng, T.W. et al., Area Effect of Patterned Carbon Nanotube Bundle on Field Electron Emission Characteristics, (Research Paper), 9th International Conference on Atomically Controlled Surfaces, Interfaces and Nanostructures 2007, Sep. 30, 2008, pp. 7755-7758, vol. 254, No. 23.

* cited by examiner

ASYMMETRICAL-NANOFINGER DEVICE FOR SURFACE-ENHANCED LUMINESCENSE

GOVERNMENT INTEREST

Subject matter described herein was made with government support under Contract No. HR0011-09-3-0002 awarded by Defense Advanced Research Projects Agency (DARPA). The government has certain rights in the described subject matter.

RELATED APPLICATIONS

This Application is related to PCT Patent Application, Serial Number PCT/US10/31790 by Zhiyong Li, et al., filed on Apr. 20, 2010, entitled "MULTI-PILLAR STRUCTURE FOR MOLECULAR ANALYSIS," and assigned to the assignee of the present technology. This Application is also related to PCT Patent Application, Serial Number PCT/US10/31809 by Zhiyong Li, et al., filed on Apr. 20, 2010, entitled "A SELF-ARRANGING, LUMINESCENCE-ENHANCEMENT DEVICE FOR SURFACE-ENHANCED LUMINESCENCE," and assigned to the assignee of the present technology.

TECHNICAL FIELD

Embodiments of the present technology relate generally to devices for surface-enhanced luminescence.

BACKGROUND

Surface-enhanced luminescence techniques, such as surface-enhanced Raman spectroscopy (SERS), have emerged as leading-edge techniques for the analysis of the structure of inorganic materials and complex organic molecules. For example, in SERS, scientists engaged in the application of Raman spectroscopy have found that by decorating a surface, upon which a molecule is later adsorbed, with a thin layer of a metal in which surface plasmons have frequencies in a range of electromagnetic radiation used to excite such a molecule and in which surface plasmons have frequencies in a range of electromagnetic radiation emitted by such a molecule, it is possible to enhance the intensity of a Raman spectrum of such a molecule.

In addition, spectroscopists utilizing spectroscopic techniques for the analysis of molecular structures have a continuing interest in improving the sensitivity of their spectroscopic techniques. Not only is improved sensitivity desirable for reducing the time of analysis, but also improved sensitivity can provide previously unachievable results. For example, improved sensitivity is directly related to lower detectability limits for previously undetected molecular constituents. Thus, scientists engaged in the application of surface-enhanced luminescence techniques are motivated to improve the sensitivity of surface-enhanced luminescence techniques, for example, SERS, for the detection of molecules and the spectral signatures of moieties in these molecules.

DESCRIPTION OF THE DRAWINGS

The accompanying drawings, which are incorporated in and form a part of this specification, illustrate examples of the technology and, together with the description, serve to explain the examples of the technology.

Figure 1:
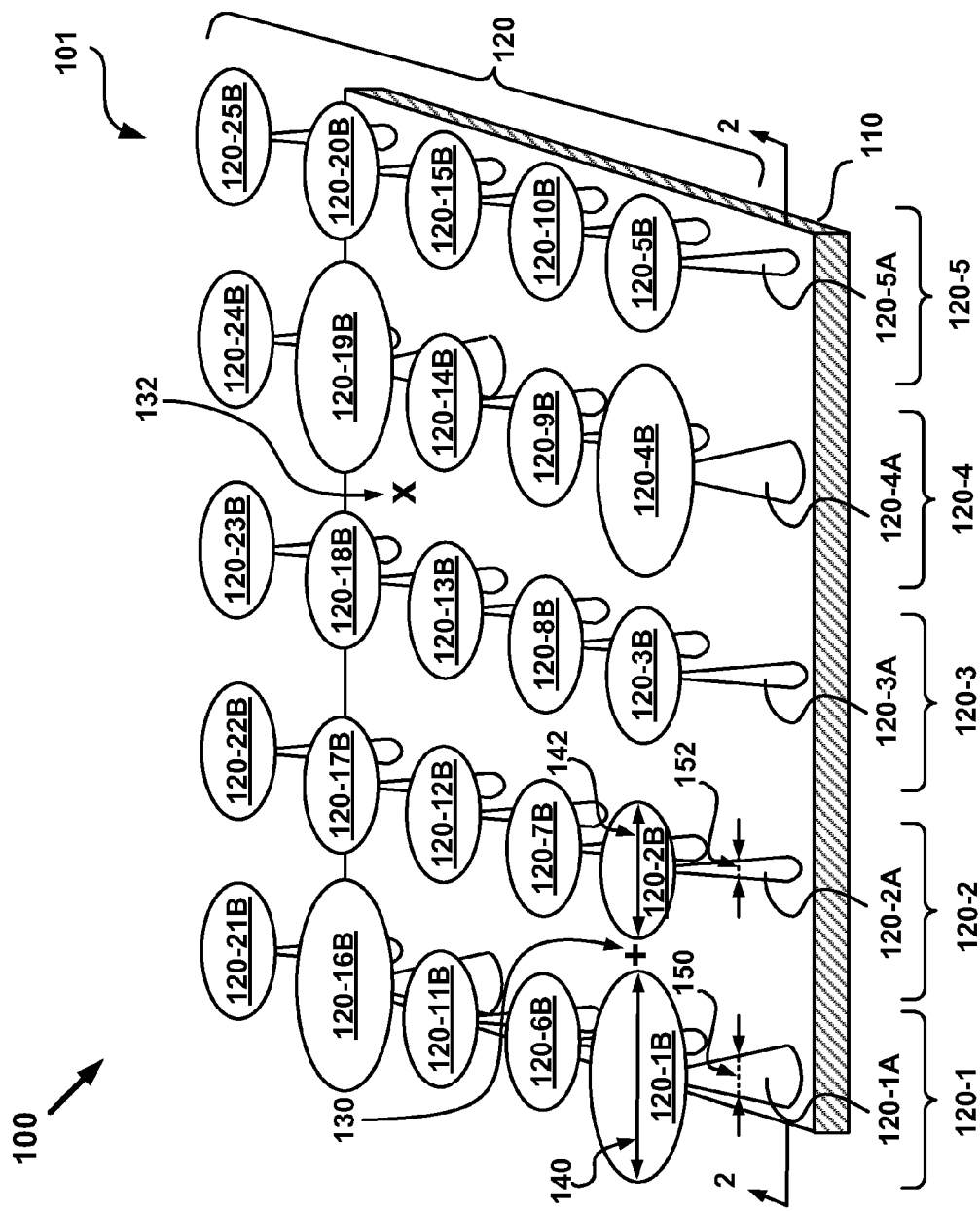
FIG. 1 is a perspective view of an asymmetrical-nanofinger device for surface-enhanced luminescence, in accordance with examples of the present technology.

The drawings referred to in this description should not be understood as being drawn to scale except if specifically noted.

DESCRIPTION OF EMBODIMENTS

Reference will now be made in detail to the alternative examples of the present technology. While the technology will be described in conjunction with the alternative examples, it will be understood that they are not intended to limit the technology to these examples. On the contrary, the technology is intended to cover alternatives, modifications and equivalents, which may be included within the spirit and scope of the technology as defined by the appended claims.

Furthermore, in the following description of examples of the present technology, numerous specific details are set forth in order to provide a thorough understanding of the present technology. However, it should be noted that examples of the present technology may be practiced without these specific details. In other instances, well known methods, procedures, and components have not been described in detail as not to unnecessarily obscure examples of the present technology. Throughout the drawings, like components are denoted by like reference numerals, and repetitive descriptions are omitted for clarity of explanation if not necessary. As used herein, the articles, "a" and "an," will also be understood as including the plural referents. Also, as used herein, the article, "the," and "said" will also be understood as including the plural referents.

Examples of the present technology include an asymmetrical-nanofinger device for surface-enhanced luminescence. The asymmetrical-nanofinger device for surface-enhanced luminescence includes a substrate, and a plurality of nanofingers coupled with the substrate. The plurality of nanofingers includes at least one primary nanofinger having a primary active-material cap, and at least one secondary nanofinger having a secondary active-material cap. A nanofinger of the plurality includes a flexible column, and an active-material cap coupled to a tip of the flexible column. An average diameter of the primary active-material cap is substantially greater than an average diameter of the secondary active-material cap. At least the primary nanofinger and at least the secondary nanofinger of the plurality of nanofingers are to self-arrange into a close-packed configuration with at least one analyte molecule disposed between at least the primary active-material cap and at least the secondary active-material cap. Examples of the present technology also include a method for fabricating the asymmetrical-nanofinger device, and an optical apparatus including an optical component that includes the asymmetrical-nanofinger device.

With reference now to FIG. 1, in accordance with examples of the present technology, a perspective view 100 is shown of an asymmetrical-nanofinger device 101 for surface-enhanced luminescence. The asymmetrical-nanofinger device 101 for surface-enhanced luminescence includes a substrate 110, and a plurality 120 of nanofingers, for example, nanofingers 120-1, 120-2, 120-3, 120-4 and 120-5, coupled with the substrate 110. The plurality 120 of nanofingers includes at least one primary nanofinger 120-1 of the plurality 120 having a primary active-material cap 120-1B, and at least one secondary nanofinger 120-2 of the plurality 120 having a secondary active-material cap 120-2B. A primary nanofinger 120-1 of the plurality 120 includes a primary flexible column 120-1A, and a primary active-material cap 120-1B. Similarly, other nanofingers, for example, nanofingers 120-2, 120-3, 120-4 and 120-5, of the plurality 120 include flexible columns, for example, flexible columns 120-2A, 120-3A, 120-4A and 120-5A, respectively, and active-material caps, for example, active-material caps 120-2B, 120-3B, 120-4B and 120-5B, respectively. Thus, secondary nanofinger 120-2 of the plurality 120 includes a secondary flexible column 120-2A, and a secondary active-material cap 120-2B.

As shown in FIG. 1, by way of example, a row of nanofingers includes nanofingers 120-1, 120-2, 120-3, 120-4 and 120-5, without limitation thereto; and, by way of example, an array of nanofingers includes several rows, without limitation thereto. Thus, in accordance with one example of the present technology, the plurality 120 of nanofingers includes the array of nanofingers including several rows of nanofingers. However, other arrangements of nanofingers that are less well-ordered than shown in FIG. 1 are also within the spirit and scope of examples of the present technology. The arrangement shown in FIG. 1 is illustrative of but one example of an arrangement of the plurality 120 of nanofingers in an asymmetrical-nanofinger device 101 as may be fabricated in a top-down fabrication procedure, which employs a reticulated mask in a photolithographic process; but, other methods of fabrication are also within the spirit and scope of examples of the present technology, which are subsequently described.

With further reference to FIG. 1, in accordance with examples of the present technology, the nanofingers in the plurality 120 of nanofingers have active-material caps, for example, active-material caps 120-1B through 120-25B, that may have different average diameters. As shown in FIG. 1, active-material caps 120-1B, 120-4B, 120-16B and 120-19B have an average diameter substantially greater than an average diameter of active-material caps 120-2B, 120-3B, 120-5B through 120-15B, 120-17B, 120-18B, and 120-20B through 120-25B. In particular, in accordance with one example of the present technology, by way of example without limitation thereto, an average diameter 140 of the primary active-material cap 120-1B is substantially greater than an average diameter 142 of the secondary active-material cap 120-2B. Similarly, in one example of the present technology, by way of example without limitation thereto, an average diameter 150 of the primary flexible column 120-1A is substantially greater than an average diameter 152 of the secondary flexible column 120-2A.

Figure 2:
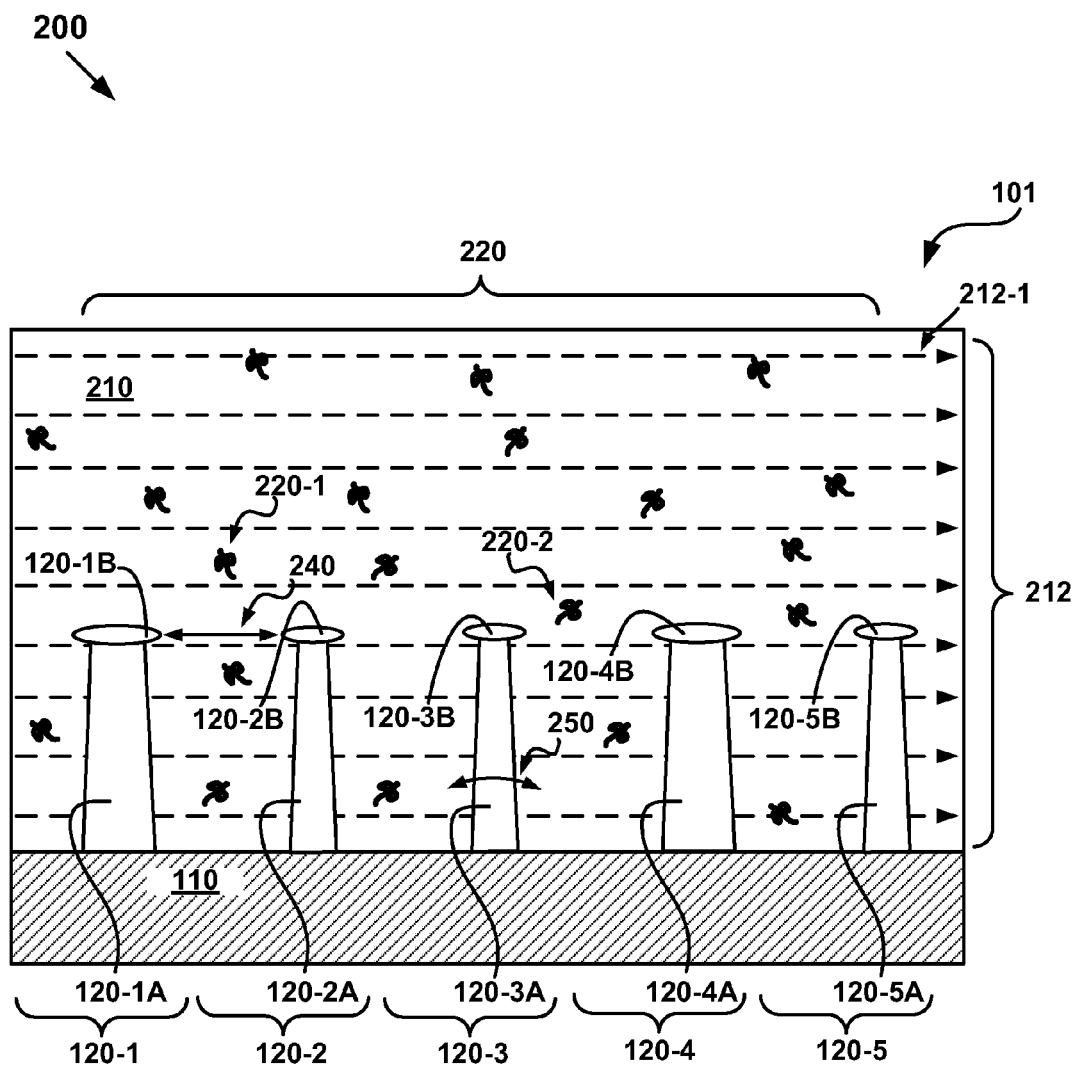
FIG. 2 is a cross-sectional elevation view, through line 2-2 of FIG. 1, of the asymmetrical-nanofinger device for surface-enhanced luminescence in contact with a fluid carrier carrying a plurality of molecules, in accordance with examples of the present technology.
Figure 3:
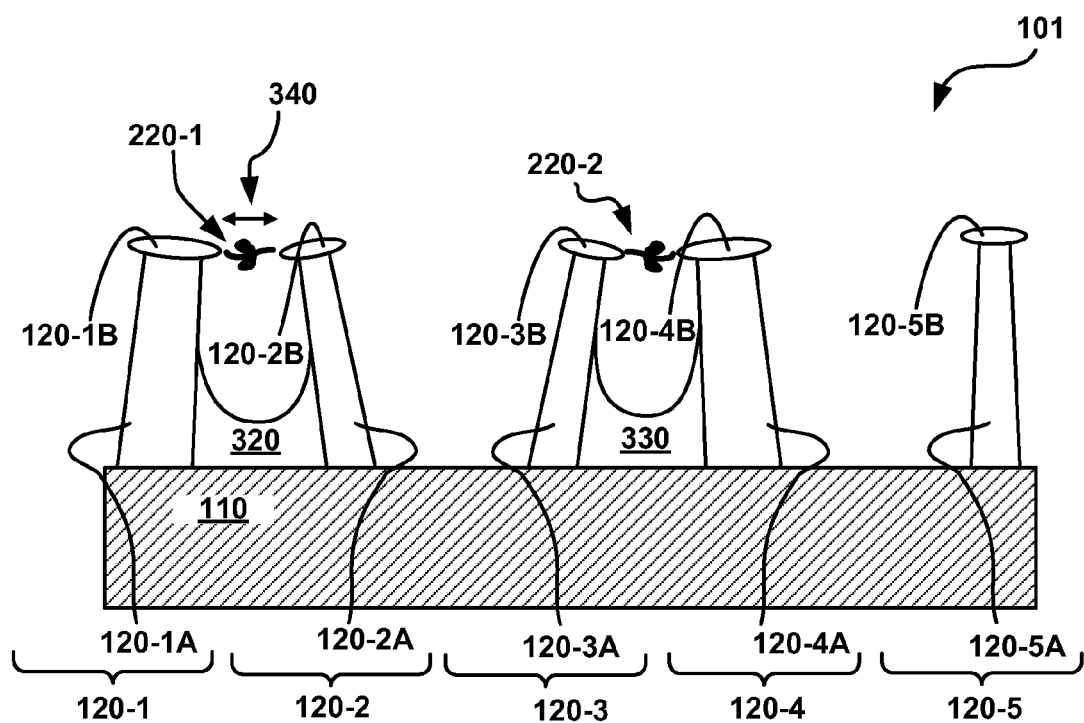
FIG. 3 is a cross-sectional elevation view, through line 2-2 of FIG. 1, of the asymmetrical-nanofinger device for surface-enhanced luminescence that shows nanofingers self-arranging into close-packed configurations with molecules disposed between active-material caps of nanofingers, in accordance with examples of the present technology.
Figure 5:
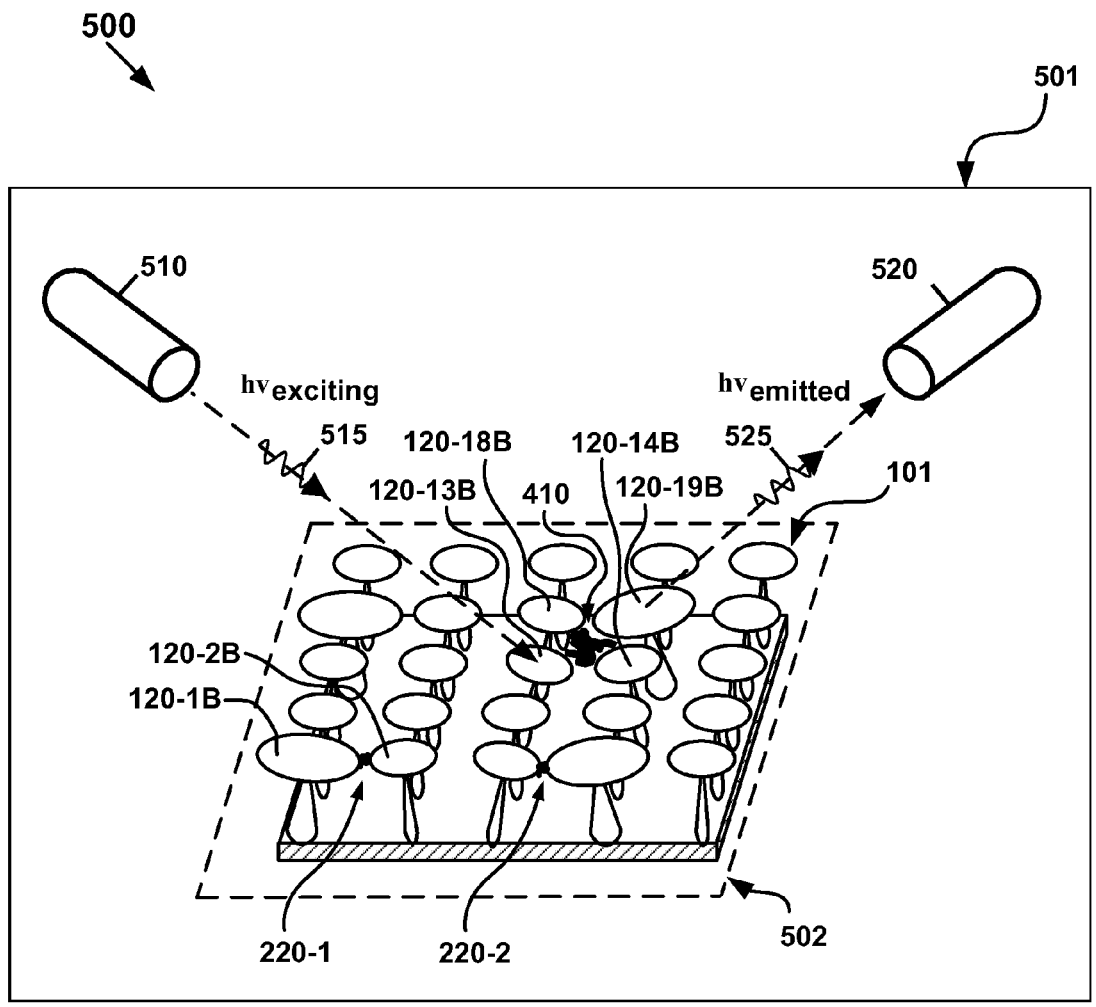
FIG. 5 is a schematic diagram of an optical apparatus including an optical component that includes the asymmetrical-nanofinger device for surface-enhanced luminescence of FIG. 1, which shows an example configuration for surface-enhanced Raman spectroscopy (SERS) of molecules disposed between the active-material caps, in accordance with examples of the present technology.
Figure 6:
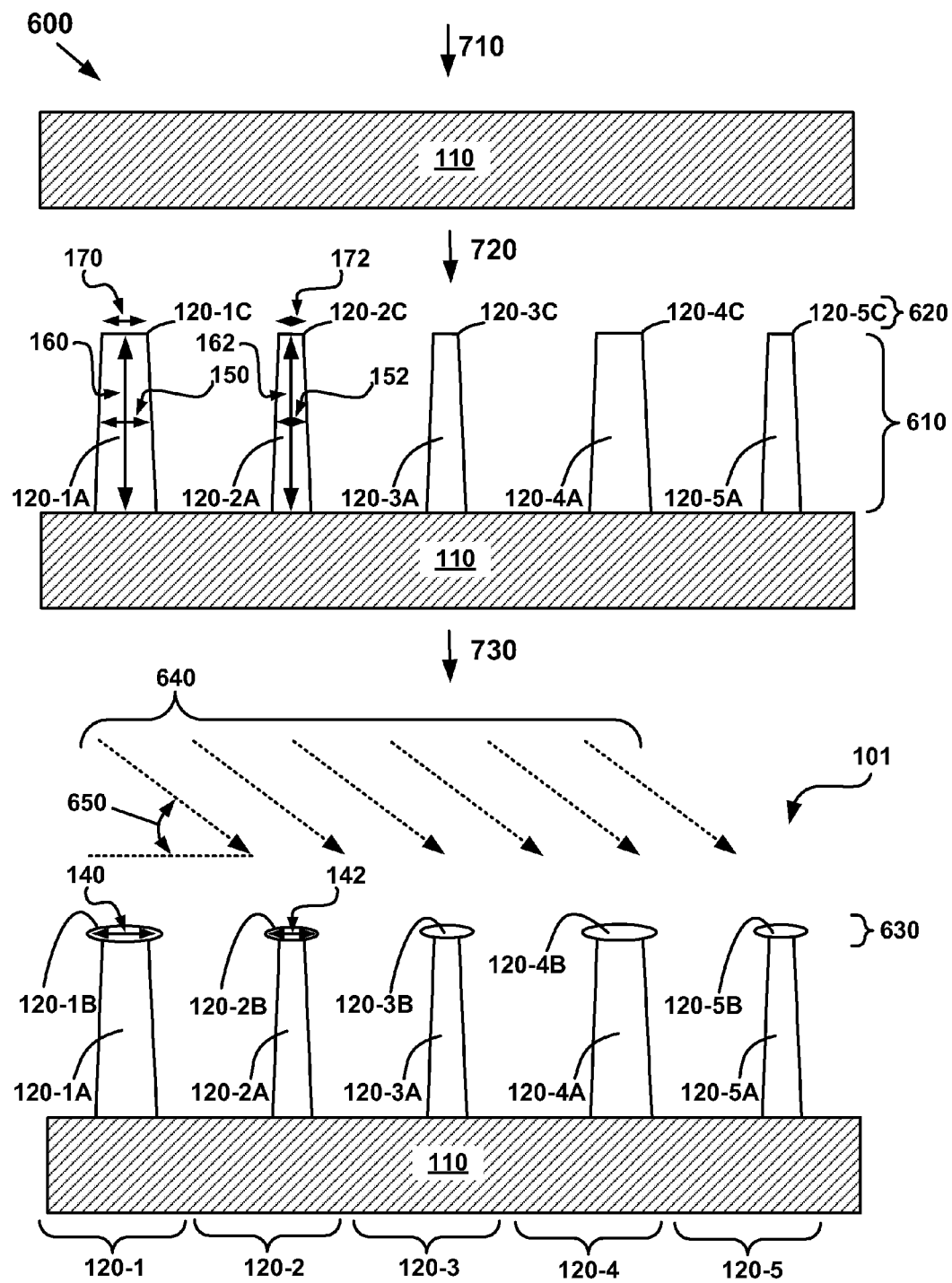
FIG. 6 is a schematic diagram showing an example sequence of processing operations used in fabrication of the asymmetrical-nanofinger device for surface-enhanced luminescence of FIG. 1, as a sequence of cross-sectional elevation views, through line 2-2 of FIG. 1, at various stages in its fabrication, in accordance with examples of the present technology.

Although, by way of example without limitation thereto, the diameters of the active-material caps, for example, active-material caps 120-1B through 120-5B, are shown as being substantially greater than respective diameters of tips of their respective flexible columns, for example, respective flexible columns 120-1A through 120-5A, in accordance with examples of the present technology, the diameter of an active-material cap may be only slightly larger than a diameter of a tip of its respective flexible column, for example, as shown in FIGS. 2, 3 and 6. In accordance with examples of the present technology, a diameter of an active-material cap that is only slightly larger than a diameter of a tip of its respective flexible column may be fabricated, as subsequently described in the discussion of FIG. 6, by the deposition of thin films of active material having thickness on the order of a few nanometers to a few tens of nanometers on the tips of respective flexible columns to produce active-material caps with a disk-like shape, by way of example without limitation thereto. Thus, in FIGS. 1-6 the active-material caps are shown having an ellipsoidal shape suggestive of a disk-like shape, which is by way of example without limitation thereto, as other shapes of active-material caps are also within the spirit and scope of examples of the present technology.

As described herein, the term of art, "primary," refers to nanofingers, active-material caps, tips, and flexible columns of respective nanofingers that have a respective active-material cap with an average diameter substantially greater than an average diameter of a secondary active-material cap; and, the term of art, "secondary," refers to nanofingers, active-material caps, tips, and flexible columns of respective nanofingers that have a respective active-material cap with an average diameter substantially lesser than an average diameter of a primary active-material cap. Thus, active-material caps 120-1B, 120-4B, 120-16B and 120-19B may be referred to herein as primary active-material caps; and, active-material caps 120-2B, 120-3B, 120-5B through 120-15B, 120-17B, 120-18B, and 120-20B through 120-25B may be referred to herein as secondary active-material caps. Similarly, of the flexible columns labeled in FIG. 1, so as not to make the figure overly busy, flexible columns 120-1B and 120-4B may be referred to herein as primary flexible columns; and, flexible columns 120-2B, 120-3B and 120-5B may be referred to herein as secondary flexible columns.

In addition, as described herein, the term of art, "substantially greater than," refers to a dimension of a component part of a nanofinger, for example, a flexible column, or an active-material cap, that is greater than a corresponding dimension of a corresponding component part of another nanofinger, with which it is compared, by an amount that is greater than the variability of the dimension of the component part expected due to statistical variations alone of a dimension of a component part fabricated to have a constant dimension in an associated manufacturing process. Conversely, as described herein, "substantially lesser than," refers to a dimension of a component part of a nanofinger, for example, a flexible column, or an active-material cap, that is less than a corresponding dimension of a corresponding component part of another nanofinger, with which it is compared, by an absolute amount that is greater than the variability of the dimension of the component part expected due to statistical variations alone of a dimension of a component part fabricated to have a constant dimension in an associated manufacturing process.

Therefore, in accordance with another example of the present technology, the respective component parts of the plurality 120 of nanofingers may be fabricated not having all of certain dimensions made uniformly constant, for example, average diameters of all the active-material caps; but rather, the plurality 120 of nanofingers may be fabricated to include at least two populations of nanofingers: at least a plurality of primary nanofingers, and at least a plurality of secondary nanofingers. Thus, as certain dimensions of component parts of the plurality of primary nanofingers is substantially greater than certain corresponding dimensions of corresponding component parts of the plurality of secondary nanofingers, the inventor has used the figurative term of art, "asymmetrical-nanofinger," to describe examples of the present technology for the asymmetrical-nanofinger device. On the other hand, with reference to FIG. 6, in accordance with an example of the present technology, by way of example without limitation thereto, an average height 160 of the primary flexible column 120-1A may be about equal to an average height 162 of the secondary flexible column 120-2A.

Figure 4:
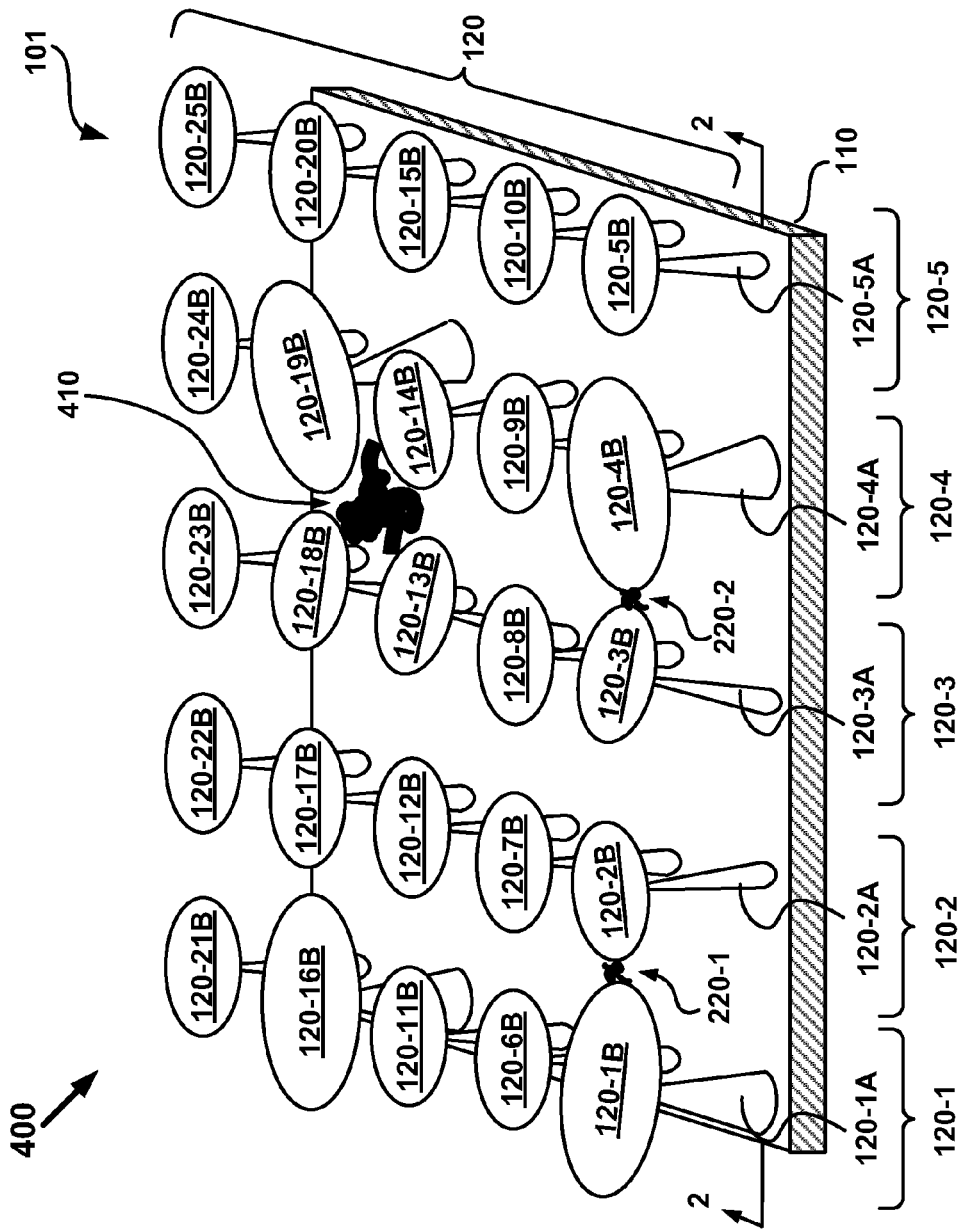
FIG. 4 is another perspective view of the asymmetrical-nanofinger device for surface-enhanced luminescence of FIG. 1 after the nanofingers have self-arranged into close-packed configurations with molecules disposed between the active-material caps, in accordance with examples of the present technology.

With further reference to FIG. 1, in accordance with examples of the present technology, a nanofinger, for example, primary nanofinger 120-1, of the plurality 120 of nanofingers is shown with a shape resembling what may be figuratively described as, a "mushroom," which is by way of example without limitation thereto. However, in accordance with examples of the present technology, a nanofinger is not limited to having such a shape, as other shapes are also within the spirit and scope of examples of the present technology. Moreover, by way of example, in accordance with examples of the present technology, the flexible columns may have the form of nanocones, as shown in FIGS. 1 and 4, without limitation thereto; but, more generally, the flexible columns may be selected from the group consisting of: nanocones, nanopyramids, nanorods, nanobars, nanopoles and nanograss, without limitation thereto. As used herein, the terms of art, "nanocones, nanopyramids, nanorods, nanobars, nanopoles and nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nano-columns having the following dimensions: a diameter of 50 nm to 500 nm, a height of 50 nm to 2 micrometers (µm), and a gap between flexible columns of 20 nm to 500 nm. The terms of art, substantially conical, substantially pyramidal, substantially rod-like, substantially bar-like, substantially pole-like and substantially grass-like, means that the structures have nearly the respective shapes of cones, pyramids, rods, bars, poles and grass-like asperities within the limits of fabrication with nanotechnology.

Furthermore, by way of example, in accordance with examples of the present technology, the active-material caps may have the form of oblate nanospheroids, as shown in FIGS. 1 and 4, without limitation thereto; but, more generally, the active-material caps may be selected from the group consisting of: nanospheres, prolate nanospheroids, oblate nanospheroids, nanodisks, and nanoplates, without limitation thereto. As used herein, the terms of art, "nanospheres, prolate nanospheroids, oblate nanospheroids, nanodisks, and nanoplates," refer to structures that are substantially: spherical, prolate spheroidal, oblate spheroidal, disk-like, and plate-like, respectively, which have nano-dimensions as small as a few nanometers in size: height, diameter, or width. For example, in accordance with examples of the present technology, the diameter of the active-material caps is on the order of 20 nm to 500 nm. In addition, the terms of art, substantially spherical, substantially prolate spheroidal, substantially oblate spheroidal, substantially disk-like, and substantially and plate-like, means that the structures have nearly the respective shapes of spheres, prolate spheroids, oblate spheroids, disks, and plates within the limits of fabrication with nanotechnology. Thus, in accordance with one example of the present technology, a shape of the primary active-material cap 120-1B may be substantially spherical. Similarly, in accordance with another example of the present technology, a shape of the secondary active-material cap 120-2B may also be substantially spherical.

With further reference to FIG. 1, in accordance with examples of the present technology, the primary active-material cap 120-1B is coupled to a primary tip 120-1C (not shown in FIG. 1, but see FIG. 6) of the primary flexible column 120-1A. Similarly, other active-material caps, for example, active-material caps 120-2B, 120-3B, 120-4B and 120-5B, are coupled to tips, for example, tips 120-2C, 120-3C, 120-4C and 120-5C, respectively, (not shown in FIG. 1, but see FIG. 6) of flexible columns, for example, flexible columns 120-2A, 120-3A, 120-4A and 120-5A, respectively. Thus, in accordance with examples of the present technology, the secondary active-material cap 120-2B is coupled to a secondary tip 120-2C (not shown in FIG. 1, but see FIG. 6) of the secondary flexible column 120-2A.

With further reference to FIG. 1, in accordance with examples of the present technology, at least one primary active-material cap 120-1B of a plurality 630 of active-material caps may be disposed adjacent to secondary active-material caps 120-2B, 120-6B, 120-7B that are disposed as satellites proximate to the primary active-material cap 120-1B. By way of example without limitation thereto, primary active-material cap 120-19B is surrounded by secondary active-material caps 120-13B, 120-14B, 120-15B, 120-20B, 120-25B, 120-24B, 120-23B and 120-18B that are disposed as satellites proximate to the primary active-material cap 120-19B. In this regard, secondary active-material caps 120-14B, 120-20B, 120-24B and 120-18B are disposed as first nearest neighbors to the primary active-material cap 120-19B; and, secondary active-material caps 120-13B, 120-15B, 120-25B, and 120-23B are disposed as second nearest neighbors to the primary active-material cap 120-19B. Similarly, by way of example without limitation thereto, primary active-material cap 120-4B is partially surrounded by secondary active-material caps 120-3B, 120-8B, 120-9B, 120-10B and 120-5B that are disposed as satellites proximate to the primary active-material cap 120-4B. Also, by way of example without limitation thereto, primary active-material cap 120-16B is disposed adjacent to secondary active-material caps 120-11B, 120-12B, 120-17B, 120-22B and 120-21B that are disposed as satellites proximate to the primary active-material cap 120-16B. Although the plurality 630 (See FIG. 6) of active-material caps is shown arranged in a square lattice, this is by way of example, without limitation thereto as other arrangements are also within the spirit and scope of examples of the present technology.

With further reference to FIG. 1, in accordance with examples of the present technology, a plurality of interstices is disposed between active-material caps of the plurality 120 of nanofingers. For example, a small interstice 130 is located between primary active-material cap 120-1B and secondary active-material cap 120-2B. By way of further example, an interstice of a different kind, a large interstice 132, is located between four active-material caps: secondary active-material caps 120-13B, 120-14B and 120-18B, and primary active-material cap 120-19B. Such interstices are to receive molecules (not shown, but see FIG. 2) for the purpose of surface-enhanced luminescence.

As used herein, the term of art, "surface-enhanced luminescence," also embraces within the scope of its meaning surface-enhanced Raman emission, as in surface-enhanced Raman spectroscopy (SERS), and surface-enhanced fluorescence. In accordance with examples of the present technology, at least one primary active-material cap 120-1B of a plurality 630 (see FIG. 6) of active-material caps is to enhance luminescence from a molecule 220-1 (not shown, but see FIG. 2) disposed in close proximity to the primary active-material cap 120-1B. In accordance with examples of the present technology, at least the primary nanofinger 120-1 and a secondary nanofinger 120-2 of the plurality 120 are to self-arrange into a close-packed configuration with at least one molecule 220-1 (not shown, but see FIG. 2) disposed between at least the primary active-material cap 120-1B and a secondary active-material cap 120-2B of respectively primary nanofinger 120-1 and secondary nanofinger 120-2, for example, at the location of the small interstice 130, as is next described with the aid of a cross-section through line 2-2.

With reference now to FIG. 2, in accordance with examples of the present technology, a cross-sectional elevation view 200 is shown of the asymmetrical-nanofinger device 101 through line 2-2 of FIG. 1. FIG. 2 shows a row of nanofingers 120-1, 120-2, 120-3, 120-4 and 120-5 in profile; nanofingers 120-1, 120-2, 120-3, 120-4 and 120-5 include flexible columns 120-1A, 120-2A, 120-3A, 120-4A and 120-5A, and active-material caps 120-1B, 120-2B, 120-3B, 120-4B and 120-5B, respectively. As shown in FIG. 2, the range of flexibility of each of the flexible columns 120-1A, 120-2A, 120-3A, 120-4A and 120-5A is indicated by the example double headed arrow 250, which is shown overlaying flexible column 120-3A. As further shown in FIG. 2, the row of nanofingers 120-1, 120-2, 120-3, 120-4 and 120-5 of the asymmetrical-nanofinger device 101 is to come into contact with a fluid carrier 212 carrying a plurality 220 of molecules, for example, molecules 220-1 and 220-2. The fluid carrier 212 includes a fluid 210 and the plurality 220 of molecules, for example, molecules 220-1 and 220-2.

With further reference to FIG. 2, in accordance with examples of the present technology, by way of example, the fluid carrier 212 may be in motion, without limitation thereto, as indicated by flow vectors, of which flow vector 212-1 is an example; such a configuration might be suitable for sampling an environment with the asymmetrical-nanofinger device 101 for the presence of a suspect molecule. Alternatively, the fluid carrier 212 may be static without motion, as might be the case for immersion of the asymmetrical-nanofinger device 101 in a solution, including the fluid carrier 212, containing an analyte and the fluid 210 and molecules of which the analyte is composed. In accordance with examples of the present technology, the term of art, "fluid," is used in a general sense so that the fluid 210 may be a liquid, or alternatively, a gas. Thus, the asymmetrical-nanofinger device 101 is to receive molecules of an analyte for spectroscopic analysis as is SERS, surface-enhanced fluorescence spectroscopy, or other surface-enhanced luminescence applications.

With further reference to FIG. 2, in accordance with examples of the present technology, an analyte molecule 220-1 may approach the site of an interstice, for example, interstice 130, where adjacent active-material caps, for example, primary active-material cap 120-1B and secondary active-material cap 120-2B, are separated by a distance 240. In accordance with an example of the present technology, an active-material cap, for example, secondary active-material cap 120-2B, of the plurality 120 of nanofingers is to bind to a molecule 220-1 disposed in close proximity to the secondary active-material cap 120-2B. By way of example, such binding may occur through Van der Waals forces between the secondary active-material cap 120-2B and the molecule 220-1, without limitation thereto; or alternatively, such binding may occur through other types of binding forces, such as surface physisorption or surface chemisorption of the molecule by the secondary active-material cap 120-2B, without limitation thereto. Once the molecule is bound to an active-material cap, for example, secondary active-material cap 120-2B, and/or primary active-material cap 120-1B, in accordance with an example of the present technology, at least one active-material cap, for example, secondary active-material cap 120-2B, and/or primary active-material cap 120-1B, of a plurality 630 (see FIG. 6) of active-material caps is to enhance luminescence from the molecule 220-1 disposed in close proximity to the secondary active-material cap 120-2B, and/or primary active-material cap 120-1B.

Moreover, in accordance with another example of the present technology, at least one active-material cap, for example, secondary active-material cap 120-2B, and/or primary active-material cap 120-1B, of the plurality 630 (see FIG. 6) of active-material caps may be composed of a constituent that enhances surface luminescence, such as an active material selected from the group consisting of copper (Cu), silver (Ag), aluminum (Al), platinum (Pt) and gold (Au), or any combination of Cu, Ag, Al, Pt and Au, without limitation thereto. As used herein, the term of art, "active-material," refers to a material that can support formation of surface plasmons in an active-material cap, for example, a primary active-material cap 120-1B, and/or a secondary active-material cap 120-2B, to enhance the local electromagnetic field for surface-enhanced luminescence, as for example, in SERS, without limitation thereto. In accordance with another example of the present technology, at least one primary active-material cap 120-1B, and/or secondary active-material cap 120-2B, of the plurality 630 of active-material caps may include a layered structure including a plurality of metallic layers, such that a metallic layer of the plurality of metallic layers is composed of a constituent selected from the group consisting of Cu, Ag, Al, Pt and Au, or any combination of Cu, Ag, Al, Pt and Au.

Furthermore, in accordance with another example of the present technology, the flexible columns 120-1A, 120-2A, 120-3A, 120-4A and 120-5A of the plurality 120 of nanofingers 120-1, 120-2, 120-3, 120-4 and 120-5 further include a flexible material selected from the group, which includes both dielectric and non-dielectric materials, consisting of a highly cross-linked uv-curable or thermal-curable polymer, a highly cross-linked uv-curable or thermal-curable plastic, a polysiloxane compound, silicon, silicon dioxide, spin-on glass, a sol-gel material, silicon nitride, diamond, diamond-like carbon, aluminum oxide, sapphire, zinc oxide, and titanium dioxide, the purpose of which is next described.

With reference now to FIG. 3, in accordance with examples of the present technology, a cross-sectional elevation view 300 is shown of the asymmetrical-nanofinger device 101 through line 2-2 of FIG. 1. FIG. 3 shows nanofingers 120-1, 120-2, 120-3 and 120-4 self-arranging into close-packed configurations with molecules, for example, molecule 220-1, disposed between primary active-material cap 120-1B of primary nanofinger 120-1 and secondary active-material cap 120-2B of secondary nanofinger 120-2, and, for example, molecule 220-2, disposed between primary active-material cap 120-4B of primary nanofinger 120-4 and secondary active-material cap 120-3B of secondary nanofinger 120-3. Because the flexible columns 120-1A, 120-2A, 120-3A and 120-4A of the plurality 120 of nanofingers include a flexible, or compliant, material as described above, in accordance with an example of the present technology, at least one secondary flexible column 120-2A is to bend towards at least a primary flexible column 120-1A, and to dispose the molecule 220-1 in close proximity with at least the primary active-material cap 120-1B on the primary flexible column 120-1A. Alternatively, at least one primary flexible column 120-1A may bend towards at least a secondary flexible column 120-1A, and dispose a molecule, such as molecule 220-1, in close proximity with at least the secondary active-material cap 120-2B on the secondary flexible column 120-2A. However, as a primary flexible column has a substantially larger diameter than a secondary flexible column, the secondary flexible column is expected to be more compliant and bend easier than the primary flexible column.

In the case where the fluid carrier 212 includes a liquid, small amounts of liquid, for example, liquid pools 320 and 330, may remain trapped between the flexible columns, for example, primary flexible column 120-1A and secondary flexible column 120-2A, and secondary flexible column 120-3A and primary flexible column 120-4A, respectively, which give rise to microcapillary forces exerted upon the flexible columns; the microcapillary forces serve to draw together the flexible columns, for example, primary flexible column 120-1A and secondary flexible column 120-2A, and secondary flexible column 120-3A and primary flexible column 120-4A, as the liquid evaporates. For example, evaporation of the liquid from liquid pool 320 allows the primary nanofinger 120-1 and secondary nanofinger 120-2 to self-arrange into a close-packed configuration with at least one molecule 220-1 disposed between at least the primary active-material cap 120-1B and the secondary active-material cap 120-2B of respectively primary nanofinger 120-1 and secondary nanofinger 120-2.

Thus, with further reference to FIGS. 2 and 3, in the case where the fluid carrier 212 includes a liquid, in accordance with examples of the present technology, at least the secondary flexible column 120-1A is to bend towards the primary flexible column 120-1A under action of microcapillary forces induced by removal of the fluid 210, a liquid, provided to carry the molecule 220-1 into proximity with the primary active-material cap 120-1B and secondary active-material cap 120-2B. In accordance with another example of the present technology, a spacing 340 of the close-packed configuration between the primary active-material cap 120-1B and secondary active-material cap 120-2B with a molecule, for example, molecule 220-1, disposed between the primary active-material cap 120-1B and secondary active-material cap 120-2B is determined by a balance of binding forces, between the molecule 220-1 and the primary active-material cap 120-1B and secondary active-material cap 120-2B, with restoring forces exerted by at least the secondary flexible column 120-2A due to displacement of the secondary flexible column 120-2A towards the primary flexible column 120-1A. Thus, in accordance with an example of the present technology, the spacing 340 approaches a limit determined by the size of the molecule 220-1, which may be as small as 0.5 nm; the spacing 340 approaches the physical limit of the smallest possible separation between primary active-material cap 120-1B and secondary active-material cap 120-2B. The close proximity of the primary active-material cap 120-1B to the secondary active-material cap 120-2B enables the active-material caps act as two antennas approaching the largest coupling that may be possible between at least two such antennas for surface-enhanced luminescence. Moreover, the effect of coupling more than two active-material caps acting as antennas is also within the spirit and scope examples of the present technology, which is next described.

With reference now to FIG. 4 and further reference to FIGS. 1 and 3, in accordance with examples of the present technology, another perspective view 400 is shown of the asymmetrical-nanofinger device 101 of FIG. 1. As shown in FIG. 4, some of the nanofingers of the plurality 120 have self-arranged into close-packed configurations with molecules, for example, molecules 220-1, 220-2 and 410, disposed between the active-material caps, for example, primary active-material cap 120-1B and secondary active-material cap 120-2B, primary active-material cap 120-4B and secondary active-material cap 120-3B, and primary active-material cap 120-19B and secondary active-material caps 120-13B, 120-14B and 120-18B, respectively. In accordance with examples of the present technology, the corresponding flexible columns coupled with the active-material caps have bent towards adjacent flexible columns, as might occur under action of microcapillary forces induced by removal of the fluid 210, which in this case is a liquid.

For example, the small interstices, similar to interstice 130, are to capture smaller molecules, for example, molecules 220-1 and 220-2; and, the large interstices, similar to interstice 132, are to capture larger molecules, for example, molecule 410. In accordance with examples of the present technology, the size of the molecules captured is determined by the self-arranging spacing between the active-material caps, for example, the spacing 340 of the close-packed configuration between the primary active-material cap 120-1B and secondary active-material cap 120-2B with the molecule 220-1 disposed between the primary active-material cap 120-1B and secondary active-material cap 120-2B. By way of example, in accordance with examples of the present technology, the size of the self-arranging spacing may be on the order of 2 nm, without limitation thereto. Thus, in accordance with examples of the present technology, the asymmetrical-nanofinger device 101 may provide a substrate to capture molecules of various sizes from a solution carrying an analyte of at least one particular molecular species. For example, the asymmetrical-nanofinger device 101 may then be used in SERS analysis of the captured molecules of an analyte, which is next described in greater detail.

With reference now to FIG. 5 and further reference to FIGS. 1, 3 and 4, in accordance with other examples of the present technology, a schematic diagram 500 is shown of an optical apparatus 501. As shown in FIG. 5, the optical apparatus 501 includes an optical component 502 that includes the asymmetrical-nanofinger device 101 for surface-enhanced luminescence of FIG. 1. By way of example, in accordance with one example of the present technology, an example configuration is shown for SERS, without limitation thereto, of molecules disposed between the active-material caps of the asymmetrical-nanofinger device 101. In accordance with examples of the present technology, the asymmetrical-nanofinger device 101 for surface-enhanced luminescence includes a substrate 110, and a plurality 120 of nanofingers coupled with the substrate 110.

With further reference to FIGS. 5 and 1, in accordance with examples of the present technology, the plurality 120 of nanofingers includes at least one primary nanofinger 120-1 having a primary active-material cap 120-1B, and at least one secondary nanofinger 120-2 having a secondary active-material cap 120-2B. In accordance with examples of the present technology, an average diameter 140 of the primary active-material cap 120-1B is substantially greater than an average diameter 142 of the secondary active-material cap 120-2B. In accordance with examples of the present technology, at least the primary nanofinger 120-1 and at least the secondary nanofinger 120-2 of the plurality 120 of nanofingers are to self-arrange into a close-packed configuration with at least one analyte molecule 220-1 disposed between at least the primary active-material cap 120-1B and at least the secondary active-material cap 120-2B. Thus, previously described examples of the present technology for the asymmetrical-nanofinger device 101 may be incorporated within the environments of the optical component 502 and the optical apparatus 501, without limitation thereto. Moreover, in accordance with examples of the present technology, the optical component 502 may be selected from the group consisting of a mirror, a grating, a wave-guide, a cuvette, a test strip, and an analytical cell.

With further reference to FIG. 5, in accordance with examples of the present technology, the optical apparatus 501 may include a luminescence analyzer, such that the luminescence analyzer is to accept the optical component 502 for measuring surface-enhanced luminescence from a molecule, for example, molecule 410, and/or molecules 220-1 and 220-2. By way of another example, in accordance with examples of the present technology, the optical apparatus 501 may include a spectrometer, for example, a Raman spectrometer, without limitation thereto. FIG. 5 shows the configuration of the optical apparatus 501 including a spectrometer to accept the optical component 502 for performing spectroscopy, for example, SERS, of at least one molecule, for example, molecule 220-1, molecule 220-2, or molecule 410.

With further reference to FIG. 5, in accordance with examples of the present technology, the spectrometer includes a source 510 of exciting electromagnetic radiation 515 that is used to excite at least one molecule, for example, molecule 410. The source 510 of exciting electromagnetic radiation 515 may be a laser (not shown). The energy of a photon of the exciting electromagnetic radiation 515 is given by Planck's constant times the frequency of the laser source, given by: $h\nu_{exciting}$. In addition, the spectrometer includes an analyzer (not shown) and a detector 520 that are used to analyze and detect emitted electromagnetic radiation 525. The emitted electromagnetic radiation 525 emerges from the molecule 410 in response to the exciting laser source. For example, in the case of SERS, the energy of a photon of the emitted electromagnetic radiation 525 from the molecule 410 is given by Planck's constant times the frequency of the molecular source, given by: $h\nu_{emitted} = h\nu_o \pm h\Delta$, where $\nu_o$ is the frequency of the incident laser field and $\Delta$ the Raman shift, where the plus sign applies to an anti-Stokes type of Raman emission, and the minus sign to a Stokes type of Raman emission. Because of the interaction with surface plasmons excited in the plurality of active-material caps, for example, primary active-material cap 120-1B and secondary active-material cap 120-2B, primary active-material cap 120-4B and secondary active-material cap 120-3B, and primary active-material cap 120-19B and secondary active-material cap 120-13B, 120-14B and 120-18B, of the plurality of nanofingers, the magnitude of the local electric field $E_{molecule}$, at a molecule for example, molecule 220-1, molecule 220-2, or molecule 410, respectively, is enhanced compared to the incident field $E_o$ of the exciting electromagnetic radiation 515.

With further reference to FIG. 5, in accordance with examples of the present technology, a secondary active-material cap, for example, one or more of secondary active-material caps 120-2B, 120-3B, 120-5B through 120-15B, 120-17B, 120-18B, and 120-20B through 120-25B, may be tuned to a frequency of exciting electromagnetic radiation 515; and, the primary active-material cap 120-1B may be tuned to a frequency of emitted electromagnetic radiation 525. For example, as shown in FIG. 5, a photon of exciting electromagnetic radiation 515 generated by source 510 is shown as being incident upon secondary active-material cap 120-13B, where it may be absorbed generating surface plasmons that excite the emission of Raman radiation from molecule 410; and, a photon of emitted electromagnetic radiation 525 is shown as propagating from primary active-material cap 120-19B, from whence it may be detected by detector 520.

Moreover, with further reference to FIG. 5, in accordance with examples of the present technology, more than one secondary active-material cap may be tuned to the frequency of exciting electromagnetic radiation 515. For example, secondary active-material caps 120-14B and 120-18B may also be tuned to the frequency of exciting electromagnetic radiation 515 absorbing photons of exciting electromagnetic radiation 515 that are absorbed generating surface plasmons in the secondary active-material caps 120-14B and 120-18B that further excite the emission of Raman radiation from molecule 410. The effect of absorbing additional photons that generate additional plasmons that increase intensity of the excited emission of Raman radiation from a molecule, for example, molecule 410, is referred to herein by the term of art, "plasmonic focusing." Thus, at least the plurality of secondary active-material caps 120-13B, 120-14B and 120-18B may participate in a plasmonic focusing effect that excites the emission of Raman radiation from molecule 410.

For another example, with further reference to FIG. 5, in accordance with examples of the present technology, a photon (not shown) of the exciting electromagnetic radiation 515 generated by source 510 may be incident upon secondary active-material cap 120-2B, where it may be absorbed generating surface plasmons that excite the emission of Raman radiation from molecule 220-1; and, a photon of emitted electromagnetic radiation 525 may propagate from primary active-material cap 120-1B, from whence it may be detected by detector 520. In accordance with examples of the present technology, an average diameter of a secondary active-material cap, for example, average diameter 142 of secondary active-material cap 120-2B, may be tuned to a frequency of the exciting electromagnetic radiation 515; and, an average diameter of a primary active-material cap, for example, average diameter 140 of primary active-material cap 120-1B, may be tuned to a frequency of emitted electromagnetic radiation 525. For example, in accordance with one example of the present technology, an average diameter of a secondary active-material cap may be about 100 nm; and, an average diameter of a primary active-material cap may be about 500 nm to about 800 nm, which would be suitable for a Stokes type Raman emission, where the frequency of the emitted Raman electromagnetic radiation is less than the frequency of the exciting electromagnetic radiation.

In another alternative example, with further reference to FIG. 5, in accordance with examples of the present technology, a primary active-material cap, for example, one or more of primary active-material caps 120-1B 120-4B, 120-16B and 120-19B, may be tuned to a frequency of exciting electromagnetic radiation 515; and, a secondary active-material cap, for example, one or more of secondary active-material caps 120-2B, 120-3B, 120-5B through 120-15B, 120-17B, 120-18B, and 120-20B through 120-25B, may be tuned to a frequency of emitted electromagnetic radiation 525. Thus, in accordance with examples of the present technology, an average diameter of a primary active-material cap, for example, the average diameter 140 of the primary active-material cap 120-1B, may be tuned to a frequency of the exciting electromagnetic radiation 515; and an average diameter of a secondary active-material cap, for example, average diameter 142 of secondary active-material cap 120-2B, may be tuned to a frequency of the emitted electromagnetic radiation 525. For example, in accordance with one example of the present technology, an average diameter of a secondary active-material cap may be about 100 nm; and, an average diameter of a primary active-material cap may be about 500 nm to about 800 nm, which would be suitable for an anti-Stokes type Raman emission, where the frequency of the emitted Raman electromagnetic radiation is greater than the frequency of the exciting electromagnetic radiation.

With further reference to FIG. 5, in accordance with examples of the present technology, the composition of an active-material cap is such that the surface plasmons excited in the active-material cap are within the wavelength ranges of the exciting electromagnetic radiation 515 and the electromagnetic radiation emitted from the molecule 410; these wavelength ranges may extend from the near ultraviolet to the near infrared. Thus, in accordance with examples of the present technology, the plurality of active-material caps may be composed of a noble metal constituent; or alternatively, the plurality of active-material caps may be composed of a constituent selected from the group of constituents consisting of Cu, Ag, Al, Pt and Au. In accordance with an example of the present technology, the signal associated with the emitted electromagnetic radiation 525 is amplified by increasing the number of active-material caps in proximity to which a molecule is disposed. Embodiments of the present technology increase the number of active-material caps, for example, primary active-material cap 120-19B and secondary active-material caps 120-13B, 120-14B and 120-18B, in proximity to a molecule, for example, molecule 410, by employing a plurality 120 of nanofingers including a plurality 610 (see FIG. 6) of a flexible columns upon which the plurality 630 (see FIG. 6) of active-material caps are disposed. Thus, in accordance with examples of the present technology, due to the increased number of active-material caps, an increase in the excitation of surface plasmons in proximity to the molecule 410 is expected to enhance the signal from the molecule 410 in SERS. Therefore, examples of the present technology provide an asymmetrical-nanofinger device 101 for surface-enhanced luminescence, for example, for SERS, without limitation thereto.

Figure 7:
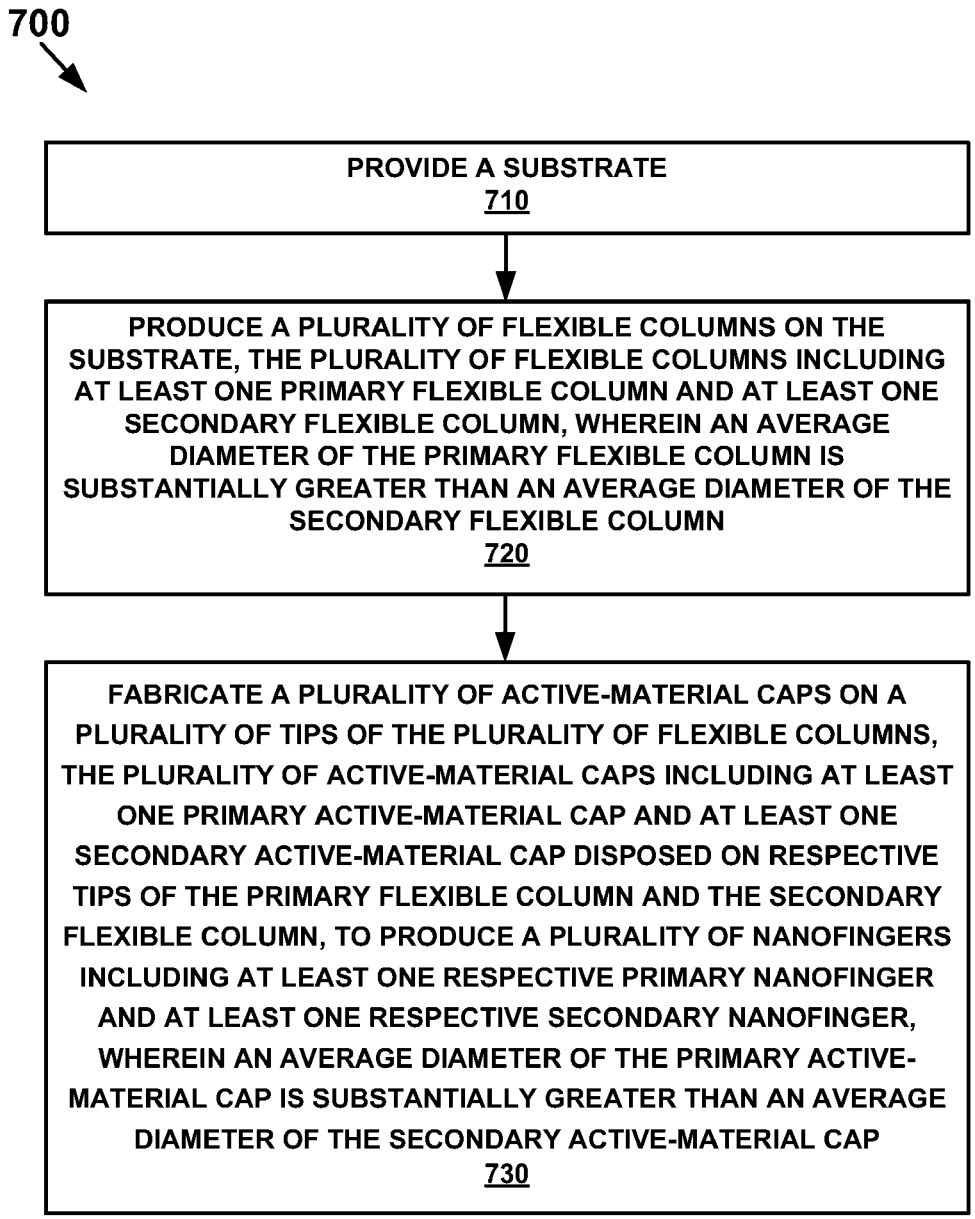
FIG. 7 is a flowchart of a method for fabricating an asymmetrical-nanofinger device for surface-enhanced luminescence, as shown in the example of FIG. 6, in accordance with examples of the present technology.

With reference now to FIGS. 6, 7 and 1, in accordance with yet other examples of the present technology, a schematic diagram 600 is shown of an example sequence of processing operations, of a method described in FIG. 7, used in fabrication of the asymmetrical-nanofinger device 101 for surface-enhanced luminescence. FIG. 6 shows the asymmetrical-nanofinger device 101 in a sequence of cross-sectional elevation views, through line 2-2 of FIG. 1, at various stages in its fabrication, corresponding to the processing operations of FIG. 7. At 710, the substrate 110 is provided upon which the rest of the structure of the asymmetrical-nanofinger device 101 is fabricated. In accordance with examples of the present technology, the substrate may be a material selected from the group consisting of silicon, glass, quartz, silicon nitride, sapphire, aluminum oxide, diamond, diamond-like carbon, one or more plastics, and one or more metals and metallic alloys. In accordance with examples of the present technology, the substrate may be in a form selected from the group consisting of a sheet, a wafer, a film and a web. For example, if the substrate is in the form of a web, the substrate may be used as feed stock, as rolls of material in a roll-to-roll fabrication process. For another example, the substrate may be in the form of a flexible polymer film composed of a plastic material, such as polyimide, polyethylene, polypropylene, or some other suitable polymeric plastic. Thus, in accordance with examples of the present technology, the substrate may be either rigid, as for a semiconductor wafer, or flexible, as for the web.

With further reference now to FIGS. 6, 7 and 1, in accordance with examples of the present technology, at 720, a cross-sectional elevation view is shown of the asymmetrical-nanofinger device 101 of FIG. 1 at an intermediate stage of fabrication. At 720, a plurality 610 of flexible columns, for example, flexible columns 120-1A, 120-2A, 120-3A, 120-4A and 120-5A, are fabricated on the substrate 110. Each of the flexible columns of the plurality 610 of flexible columns, for example, flexible columns 120-1A, 120-2A, 120-3A, 120-4A and 120-5A, includes a tip of a plurality 620 of tips, for example, tips 120-1C, 120-2C, 120-3C, 120-4C and 120-5C. In accordance with examples of the present technology, the plurality 610 of flexible columns may be produced utilizing a process selected from the group consisting of growing nanowires on the substrate 110, etching the substrate 110, nano-imprinting a coating on the substrate 110, and hot nano-embossing a coating on the substrate 110, and the laser interference lithography or photolithography technique on substrate 110. For example, in growing nanowires to produce the flexible columns, nanowire seeds are deposited onto the substrate 110, for example, silicon; and, the nanowire is grown during chemical vapor deposition from silane.

By way of another example, at 720, in etching the substrate to produce the flexible columns, a reactive ion etching (RIE) process may be applied to the substrate 110, for example, silicon; and, flexible columns, for example, in the form of nanocones, without limitation thereto, are produced by removing material from the substrate 110 through the action of reactive gaseous species, such as, fluorine, chlorine, bromine, or a halogen, in the presence of gaseous nitrogen, argon, or oxygen. By way of yet another example, at 720, in nanoimprinting the substrate to produce the flexible columns, a thermal or photo-curable thin film, for example, a highly cross-linkable resist material, is applied to the substrate 110, for example, in the form of a web, to produce a coating on the web; and, flexible columns, for example, in the form of nano-poles, without limitation thereto, are produced by rolling the web between a pair of rolls, one of which is a die having a relief pattern that is impressed into the highly viscous thin film coating of the web leaving a negative of the relief pattern of the die in the form of a plurality of nanopoles on the web, substrate 110, either through thermal or photo-curing process. By way of yet a further example, at 720, with further reference to FIG. 5, in accordance with examples of the present technology, in hot nano-embossing a coating on the substrate 110, a polymer, or plastic, is applied to the substrate 110 to produce a coating on the substrate 110; and, flexible columns, for example, in the form of nanopoles, without limitation thereto, are produced by hot embossing the coating with a die, which has a relief pattern that is impressed into the polymer, or plastic, that coats the substrate 110 leaving a negative of the relief pattern of the die in the form of a plurality of nanopoles on the substrate 110.

As shown in FIG. 6, at 720, the fabricated nanopoles may be fabricated with two different average diameters 150 and 152 depending on the diameter of corresponding features produced in the die to produce respectively primary flexible columns, for example, primary flexible columns 120-1A and 120-4A, and secondary flexible columns, for example, secondary flexible columns 120-2A, 120-3A and 120-5A. Also, the plurality 610 of flexible columns may be fabricated so that an average height 160 of a primary flexible column, for example, primary flexible column 120-1A, is about equal to an average height 162 of a secondary flexible column, for example, secondary flexible column 120-2A. By way of example, the flexible columns in FIGS. 6 and 1 are shown as having the morphology of truncated cones; but, other shapes may be produced depending upon corresponding features fabricated in the die, being also with the spirit and scope of examples of the present technology. In particular, flexible columns having the shape of pyramids, or truncated pyramids, may be fabricated. The average diameters, for example, average diameters 170 and 172, of the plurality 610 of flexible columns in proximity to the plurality 620 of tips of the plurality 610 of flexible columns provides a template that determines the subsequent respective average diameters, for example, respective average diameters 140 and 142, of the plurality 630 of active-material caps fabricated on the plurality 610 of flexible columns.

In accordance with examples of the present technology, a diameter of an active-material cap that is only slightly larger than a diameter of a tip of its respective flexible column may be fabricated, as subsequently described in the of the deposition of thin films of active material having thickness on the order of a few nanometers to a few tens of nanometers on the tips of respective flexible columns to produce active-material caps with a disk-like shape, by way of example without limitation thereto. In this way, the tips of the flexible columns provide a template for the further growth of the active-material caps, whose size is determined by both the amount of thin-film material deposited, as well as the sizes of the underlying tips of the flexible columns. Also, although the term of art, "average diameter," is used herein, this is by way of example without limitation thereto, as the term of art, "size," and/or "average lateral dimension," may also be understood to describe the various size relationships between component parts of a nanofinger, instead of "average diameter." Thus, in accordance with examples of the present technology, active-material caps of different average diameters may be fabricated, for example, a primary active-material cap 120-1B with an average diameter 140 greater than the average diameter of 142 of a secondary active-material cap 142, because the thickness of the layers of metal deposited on the plurality 620 of tips, for example, tips of truncated cones, is about the same in each of the active-material caps of the plurality 630 of active-material caps, the fabrication of which is next described.

With further reference now to FIGS. 6, 7 and 1, in accordance with examples of the present technology, at 730, a cross-sectional elevation view is shown of the asymmetrical-nanofinger device 101 of FIG. 1 nearing a final stage in fabrication. At 730, the fabrication of a plurality 120 of nanofingers, for example, nanofingers 120-1, 120-2, 120-3, 120-4 and 120-5, is completed on the substrate 110. Each of the nanofingers, for example, nanofingers 120-1, 120-2, 120-3, 120-4 and 120-5, includes a flexible column of the plurality 610 of flexible columns, for example, flexible columns 120-1A, 120-2A, 120-3A, 120-4A and 120-5A, and an active-material cap of a plurality 630 of active-material caps, for example, active-material caps 120-1B, 120-2B, 120-3B, 120-4B and 120-5B, such that each active-material cap is disposed upon a tip of the plurality 620 of tips, for example, tips 120-1C, 120-2C, 120-3C, 120-4C and 120-5C, respectively. Thus, in accordance with examples of the present technology, at least one primary nanofinger 120-1 of the plurality 120 includes the primary flexible column 120-1A that has the primary tip 120-1C coupled to the primary active-material cap 120-1B; and, at least one secondary nanofinger 120-2 of the plurality 120 includes a secondary flexible column 120-2A that has a secondary tip 120-2C coupled to the secondary active-material cap 120-2B. In accordance with examples of the present technology, the plurality 630 of active-material caps of the plurality 120 of nanofingers may be produced utilizing a process selected from the group consisting of evaporating an active-material cap, electroplating an active-material cap, precipitating an active-material cap from a colloidal suspension of metallic nanoparticles, lifting-off portions of a deposited metallic layer to form an active-material cap, and reducing adsorbed metalo-organic compounds by energetic particle bombardment to form an active-material cap.

For example, with further reference to FIGS. 6, 7 and 1, in accordance with examples of the present technology, at 730, in evaporating to produce the active-material caps, a stream of metal vapor 640 may be produced, using thin-film vacuum-evaporation techniques, to deposit metal onto the plurality 620 of tips of the plurality 610 of flexible columns 120-1A, 120-2A, 120-3A, 120-4A and 120-5A. The plurality 630 of active-material caps 120-1B, 120-2B, 120-3B, 120-4B and 120-5B are grown from the metal vapor depositing metal onto the plurality 620 of tips 120-1C, 120-2C, 120-3C, 120-4C and 120-5C of the plurality 610 of flexible columns 120-1A, 120-2A, 120-3A, 120-4A and 120-5A. In accordance with examples of the present technology, fabricating the plurality 630 of active-material caps may include evaporating metal at an angle 650 of about 90° to a surface of the substrate 110 onto a plurality 620 of tips 120-1C, 120-2C, 120-3C, 120-4C and 120-5C of the plurality 610 of flexible columns 120-1A, 120-2A, 120-3A, 120-4A and 120-5A. Alternatively, in another example of the present technology, the angle 650 may be slightly less than 90° and the substrate 110 may be rotated to provide a more uniform coating on the surface of the plurality 620 of tips 120-1C, 120-2C, 120-3C, 120-4C and 120-5C of the plurality 610 of flexible columns 120-1A, 120-2A, 120-3A, 120-4A and 120-5A. Moreover, in accordance with examples of the present technology, the size, and consequently the spacing, of the active-material caps 120-1B, 120-2B, 120-3B, 120-4B and 120-5B can be controlled by limiting the amount of material deposited from the metallic vapor during the evaporation process.

By way of another example, with further reference to FIGS. 6, 7 and 1, in accordance with examples of the present technology, at 730, in electroplating an active-material cap, the substrate 110 including the flexible columns 120-1A, 120-2A, 120-3A, 120-4A and 120-5A may be immersed in a plating solution containing metal cations. An electrical potential is applied to the substrate 110 including the flexible columns 120-1A, 120-2A, 120-3A, 120-4A and 120-5A, which results in an enhanced electrical field at the tips of the flexible columns, of which primary tip 120-1C of primary flexible column 120-1A is an example. The enhanced electrical field attracts the metal cations to the tips of the flexible columns, of which primary tip 120-1C of primary flexible column 120-1A is an example, where chemical reduction of the metal cations occurs and metal is deposited to grow the active-material caps, of which primary active-material cap 120-1B is an example.

Similarly, by way of another example, with further reference to FIGS. 6, 7 and 1, in accordance with examples of the present technology, at 730, in precipitating active-material caps from a colloidal suspension of metallic nanoparticles, the substrate 110 including the flexible columns 120-1A, 120-2A, 120-3A, 120-4A and 120-5A may be immersed in a colloidal suspension of metallic nanoparticles; an electrical potential is applied to the substrate 110 including the flexible columns 120-1A, 120-2A, 120-3A, 120-4A and 120-5A, which results in an enhanced electrical field at the tips of the flexible columns, of which primary tip 120-1C of primary flexible column 120-1A is an example; the enhanced electrical field attracts metallic nanoparticles from the colloidal suspension to the tips of the flexible columns, of which primary tip 120-1C of primary flexible column 120-1A is an example, where the metallic nanoparticles are deposited to grow the active-material caps, of which primary active-material cap 120-1B is an example.

By way of yet another example, with further reference to FIGS. 6, 7 and 1, at 730, in accordance with examples of the present technology, in a lift-off process for lifting-off portions of a deposited metallic layer to produce the active-material caps, a layer of photoresist may be applied to the substrate 110 including the flexible columns 120-1A, 120-2A, 120-3A, 120-4A and 120-5A. An undercut structure is produced in the photoresist adjacent to the sides of the columns, and the photoresist is etched away from the tips 120-1C, 120-2C, 120-3C, 120-4C and 120-5C of the flexible columns 120-1A, 120-2A, 120-3A, 120-4A and 120-5A. A stream of metal vapor 640 is deposited, using thin-film deposition techniques, for example, sputtering or evaporation, onto the plurality 620 of tips of the plurality 610 of flexible columns 120-1A, 120-2A, 120-3A, 120-4A and 120-5A. A thin film is deposited over the surface of the combined photoresist and partially fabricated asymmetrical-nanofinger device 101. The photoresist and portions of the metal layer adhering to the photoresist between the flexible columns 120-1A, 120-2A, 120-3A, 120-4A and 120-5A is then removed and the plurality 630 of active-material caps 120-1B, 120-2B, 120-3B, 120-4B and 120-5B is left adhering to the plurality 620 of tips 120-1C, 120-2C, 120-3C, 120-4C and 120-5C of the plurality 610 of flexible columns 120-1A, 120-2A, 120-3A, 120-4A and 120-5A.

By way of yet a further example, with further reference to FIGS. 6, 7 and 1, in accordance with examples of the present technology, at 730, in reducing adsorbed metalo-organic compounds by energetic particle bombardment to produce the active-material caps 120-1B, 120-2B, 120-3B, 120-4B and 120-5B, the substrate 110 including the flexible columns 120-1A, 120-2A, 120-3A, 120-4A and 120-5A may be exposed to a vapor of a chemical compound bearing a metal moiety, for example, a metalo-organic compound as used in chemical vapor deposition (CVD). For example, the metalo-organic compound may be provided in the form of a gas admitted to a vacuum chamber, such as, the vacuum chamber of a focused-ion beam (FIB) tool, a scanning electron microscope (SEM), or the target chamber of a laser ablation system, without limitation thereto. A suitable gas-injection system (GIS) interfaced to the vacuum chamber may be used to provide the chemical vapor bearing a metal moiety, for example, the metalo-organic compound. The gaseous vapor of the metalo-organic compound adsorbs on the surface of the substrate 110 including the tips 120-1C, 120-2C, 120-3C, 120-4C and 120-5C of the flexible columns 120-1A, 120-2A, 120-3A, 120-4A and 120-5A. An energetic beam of particles, for example, ions, electrons, or photons, without limitation thereto, irradiates the tips 120-1C, 120-2C, 120-3C, 120-4C and 120-5C of the flexible columns 120-1A, 120-2A, 120-3A, 120-4A and 120-5A. Such energetic beams of particles, for example, ions, electrons, or photons, without limitation thereto, may be provided, for example, by: the ion gun of a FIB tool, the electron gun of an SEM, or a laser of a laser ablation system, without limitation thereto. The energetic beam of particles, for example, ions, electrons, or photons, without limitation thereto, reduces the adsorbed gaseous vapor of the metalo-organic compound and grows the plurality 630 of active-material caps 120-1B, 120-2B, 120-3B, 120-4B and 120-5B onto the plurality 620 of tips 120-1C, 120-2C, 120-3C, 120-4C and 120-5C of the plurality 610 of flexible columns 120-1A, 120-2A, 120-3A, 120-4A and 120-5A.

With reference now to FIG. 7, in accordance with examples of the present technology, a flowchart 700 is shown of a method for fabricating an asymmetrical-nanofinger device for surface-enhanced luminescence. The method for fabricating an asymmetrical-nanofinger device for surface-enhanced luminescence includes the following. At 710, a substrate is provided. At 720, a plurality of flexible columns is produced on the substrate. In accordance with examples of the present technology, the plurality of flexible columns includes at least one primary flexible column and at least one secondary flexible column, such that an average diameter of the primary flexible column is substantially greater than an average diameter of the secondary flexible column. In accordance with examples of the present technology, producing the plurality of flexible columns on the substrate may also include a process selected from the group consisting of growing nanowires on the substrate, etching the substrate, hot nano-embossing a coating on the substrate, and nano-imprinting a coating on the substrate, as previously described.

With further reference to FIG. 7, in accordance with examples of the present technology, at 730, a plurality of active-material caps is fabricated on a plurality of tips of the plurality of flexible columns, the plurality of active-material caps includes at least one primary active-material cap and at least one secondary active-material cap disposed on respective tips of the primary flexible column and the secondary flexible column, to produce a plurality of nanofingers including at least one respective primary nanofinger and at least one respective secondary nanofinger. In accordance with examples of the present technology, an average diameter of the primary active-material cap is substantially greater than an average diameter of the secondary active-material cap. In accordance with examples of the present technology, the plurality of flexible columns are composed of a material that allows at least the primary flexible column and at least the secondary flexible column of the plurality of flexible columns to self-arrange at least the primary nanofinger and at least the secondary nanofinger into a close-packed configuration with a molecule if the molecule is disposed in proximity to at least the primary active-material cap and the secondary active-material cap, and the primary active-material cap and the secondary active-material cap are composed of a material that enhances a luminescence of the molecule if the molecule is disposed in proximity to at least one primary active-material cap and at least one secondary active-material cap.

With further reference to FIG. 7, in accordance with examples of the present technology, fabricating the plurality of active-material caps includes depositing a metal onto the plurality of tips of the plurality of flexible columns, such that a thickness of respective metallic layers of the deposited metal is substantially the same in at least one primary active-material cap and in at least one secondary active-material cap that are disposed on respective tips of the primary flexible column and the secondary flexible column. Thus, the thickness of the metallic layer of the deposited metal in the primary active-material cap is substantially equal to a respective thickness of a corresponding metallic layer of the deposited metal in the secondary active-material cap. In addition, in accordance with examples of the present technology, fabricating the plurality of active-material caps may include a process selected from the group consisting of evaporating an active-material cap, electroplating an active-material cap, precipitating an active-material cap from a colloidal suspension of metallic nanoparticles, lifting-off portions of a deposited metallic layer to form an active-material cap, and reducing adsorbed metalo-organic compounds by energetic particle bombardment to form an active-material cap, as previously described. Moreover, in accordance with examples of the present technology, fabricating the plurality of active-material caps may also include evaporating metal at an angle of about 30° to the surface of the substrate onto the plurality of tips of the plurality of flexible columns, as previously described.

Embodiments of the present technology include an asymmetrical-nanofinger device 101 that can provide enhanced sensitivity for the presence of molecules during surface-enhanced luminescence. Moreover, examples of the present technology provide for lower detectability limits for surface-enhanced luminescence of an analyte associated with a molecule in solution. For example, examples of the present technology provide for lower detectability limits in SERS analysis of a molecule. Through the tuning of the active-material caps of the asymmetrical-nanofinger device 101 to respective exciting and emitted electromagnetic radiations 515 and 525 (see FIG. 5), the sensitivity for detecting molecular species having absorption bands within which the frequency of the exciting electromagnetic radiation 515 lies and emission bands within which the emitted electromagnetic radiation 525 lies may be enhanced. In this way, examples of the present technology provide a means for selectively detecting molecular species with absorption and emission frequencies near those of the exciting and emitted electromagnetic radiations 515 and 525 (see FIG. 5), respectively. Thus, due to the enhanced selectivity, sensitivity and detectability limits for molecular detection provided by examples of the present technology, the inventor expects new applications of examples of the present technology in at least medical, environmental, chemical, and biological technologies, without limitation thereto.

The foregoing descriptions of specific examples of the present technology have been presented for purposes of illustration and description. They are not intended to be exhaustive or to limit the technology to the precise forms disclosed, and many modifications and variations are possible in light of the above teaching. The examples described herein were chosen and described in order to best explain the principles of the technology and its practical application, to thereby enable others skilled in the art to best utilize the technology and various examples with various modifications as are suited to the particular use contemplated. It may be intended that the scope of the technology be defined by the claims appended hereto and their equivalents.

What is claimed is:

1. An asymmetrical-nanofinger device for surface-enhanced luminescence, said device comprising:
    a substrate; and
    a plurality of nanofingers coupled with said substrate, comprising:
        a primary nanofinger of said plurality having a primary active-material cap; and
        a secondary nanofinger of said plurality having a secondary active-material cap;
    wherein an average diameter of said primary active-material cap is substantially greater than an average diameter of said secondary active-material cap; and
    wherein said primary nanofinger and said secondary nanofinger of said plurality of nanofingers are to self-arrange into a close-packed configuration with an analyte molecule disposed between said primary active-material cap and said secondary active-material cap.

2. The asymmetrical-nanofinger device of claim 1,
    wherein said primary active-material cap is tuned to a frequency of exciting electromagnetic radiation; and
    said secondary active-material cap is tuned to a frequency of emitted electromagnetic radiation.

3. The asymmetrical-nanofinger device of claim 1,
    wherein said secondary active-material cap is tuned to a frequency of exciting electromagnetic radiation; and
    said primary active-material cap is tuned to a frequency of emitted electromagnetic radiation.

4. The asymmetrical-nanofinger device of claim 1,
    wherein said primary nanofinger of said plurality further comprises a primary flexible column, said primary flexible column having a primary tip coupled to said primary active-material cap; and
    wherein said secondary nanofinger of said plurality further comprises a secondary flexible column, said secondary flexible column having a secondary tip coupled to said secondary active-material cap.

5. The asymmetrical-nanofinger device of claim 4,
    wherein an average diameter of said primary flexible column is substantially greater than an average diameter of said secondary flexible column.

6. The asymmetrical-nanofinger device of claim 4,
    wherein an active material of said primary active-material cap and said secondary active-material cap comprises a metal selected from the group consisting of gold, silver, copper, platinum, aluminum and combinations of gold, silver, copper, platinum, and aluminum.

7. The asymmetrical-nanofinger device of claim 1,
    wherein a shape of said primary active-material cap is substantially disk-like; and
    wherein a shape of said secondary active-material cap is substantially disk-like.

8. The asymmetrical-nanofinger device of claim 1,
    wherein said primary active-material cap of a plurality of active-material caps is surrounded by secondary active-material caps disposed as satellites proximate to said primary active-material cap.

9. The asymmetrical-nanofinger device of claim 1, wherein said primary active-material cap of a plurality of active-material caps is to enhance luminescence from a molecule disposed in close proximity to said primary active-material cap.

10. A method for fabricating an asymmetrical-nanofinger device for surface-enhanced luminescence, said method comprising:
    providing a substrate;
    producing a plurality of flexible columns on said substrate, said plurality of flexible columns comprising a primary flexible column and a secondary flexible column, wherein an average diameter of said primary flexible column is substantially greater than an average diameter of said secondary flexible column; and
    fabricating a plurality of active-material caps on a plurality of tips of said plurality of flexible columns, said plurality of active-material caps comprising a primary active-material cap and a secondary active-material cap disposed on respective tips of said primary flexible column and said secondary flexible column, to produce a plurality of nanofingers comprising a respective primary nanofinger and a respective secondary nanofinger, wherein an average diameter of said primary active-material cap is substantially greater than an average diameter of said secondary active-material cap.

11. The method of claim 10, wherein said fabricating said plurality of active-material caps comprises depositing a metal onto said plurality of tips of said plurality of flexible columns, wherein a thickness of a metallic layer of said deposited metal in said primary active-material cap is substantially equal to a respective thickness of a corresponding metallic layer of said deposited metal in said secondary active-material cap.

12. An optical apparatus, comprising:
   an optical component comprising:
      an asymmetrical-nanofinger device for surface-enhanced luminescence, said device comprising:
         a substrate; and
         a plurality of nanofingers coupled with said substrate, comprising:
            a primary nanofinger of said plurality having a primary active-material cap;
            a secondary nanofinger of said plurality having a secondary active-material cap;
         wherein an average diameter of said primary active-material cap is substantially greater than an average diameter of said secondary active-material cap; and
      wherein said primary nanofinger and said secondary nanofinger of said plurality of nanofingers are to self-arrange into a close-packed configuration with an analyte molecule disposed between said primary active-material cap and said secondary active-material cap.

13. The optical apparatus of claim 12, said optical component is selected from the group consisting of a mirror, a grating, a wave-guide, a cuvette, a test strip, and an analytical cell.

14. The optical apparatus of claim 12, further comprising:
   a spectrometer, said spectrometer to accept said optical component for performing surface-enhanced Raman spectroscopy (SERS) of said molecule.

15. The optical apparatus of claim 12, further comprising:
   a luminescence analyzer, said luminescence analyzer to accept said optical component for measuring surface-enhanced luminescence from said molecule.

\* \* \* \* \*

UNITED STATES PATENT AND TRADEMARK OFFICE
CERTIFICATE OF CORRECTION

PATENT NO. : 8,520,202 B2  
APPLICATION NO. : 13/233671  
DATED : August 27, 2013  
INVENTOR(S) : Zhiyong Li Page 1 of 1

It is certified that error appears in the above-identified patent and that said Letters Patent is hereby corrected as shown below:

On the title page, item (54), Title, and in the specifications, column 1, line 2,
delete "LUMINESCENSE" and insert -- LUMINESCENCE --, therefor.

Signed and Sealed this
Twenty-eighth Day of January, 2014

Michelle K. Lee
*Deputy Director of the United States Patent and Trademark Office*